United States Patent [19]

Kojima et al.

[11] 4,119,492

[45] Oct. 10, 1978

[54] PROCESS FOR FERMENTATIVELY PRODUCING VITAMIN $B_{12}$

[75] Inventors: Ichiro Kojima; Hiroshi Sato, both of Yokohama; Yasuo Fujiwara, Tokyo, all of Japan

[73] Assignee: Nippon Oil Company, Ltd., Japan

[21] Appl. No.: 763,539

[22] Filed: Jan. 28, 1977

[30] Foreign Application Priority Data

Feb. 5, 1976 [JP] Japan ............................ 51-10824

[51] Int. Cl.² .................................................. C12D 5/06
[52] U.S. Cl. .................................. 195/28 VB; 195/49
[58] Field of Search ......................... 195/28 VB, 49

[56] References Cited

U.S. PATENT DOCUMENTS

| | | | |
|---|---|---|---|
| 3,021,262 | 2/1962 | Perlman | 195/28 VB |
| 3,062,723 | 11/1962 | Dobry et al. | 195/28 VB |

Primary Examiner—Alvin E. Tanenholtz
Attorney, Agent, or Firm—Wenderoth, Lind & Ponack

[57] ABSTRACT

A process for producing vitamin $B_{12}$, which comprises cultivating a vitamin $B_{12}$-producing micro-organism of the genus Arthrobacter under aerobic conditions in a culture medium containing at least one compound selected from the group consisting of alcohols with 2 or 3 carbon atoms and ketones, and separating vitamin $B_{12}$ from the culture broth.

4 Claims, No Drawings

PROCESS FOR FERMENTATIVELY PRODUCING VITAMIN $B_{12}$

This invention relates to a process for producing vitamin $B_{12}$ by a fermentation technique which can afford vitamin $B_{12}$ is an improved output using vitamin $B_{12}$-producing microorganisms of the genus Arthrobacter including a novel strain. More specifically, the invention relates to a process for producing vitamin $B_{12}$ by a fermentation technique which can afford vitamin $B_{12}$ in an increased output at low cost with operational advantages using a culture medium containing specific carbon sources readily available in constant amounts. In particular, the invention relates to a process for producing vitamin $B_{12}$ by a fermentation technique which comprises cultivating a vitamin $B_{12}$-producing microorganism of the genus Arthrobacter under aerobic conditions in a culture medium containing at least one compound selected from the group consisting of alcohols with 2 or 3 carbon atoms and ketones, and recovering vitamin $B_{12}$ from the culture broth.

The existence of vitamin $B_{12}$-producing microorganisms belonging to the genus Propionibacterium, Bacillus, Corynebacterium, Arthrobacter, Rhodopseudomonas, Protaminobacter, Streptomyces, Rhodospirillum, Actinomyces, Selenomonas, and Nocardia have been known. Some of these microorganisms utilize carbohydrates as a carbon source. Some other microorganisms of the genus Corynebacterium, Arthrobacter, Pseudomonas and Nocardia are known to utilize hydrocarbons as a carbon source. Microorganisms of the genus Pseudomonas and Protaminobacter which produce vitamin $B_{12}$ by utilizing methanol, a $C_1$ alcohol, as a carbon source have been reported.

There has been no report, however, about the use of a culture medium containing a $C_2$-$C_3$ alcohol and/or a ketone as a carbon source in the production of vitamin $B_{12}$ by known vitamin $B_{12}$-producing microorganisms including those of the genus Arthrobacter utilized in the invention.

Carbohydrates are by far the most widely and commonly used carbon sources in the fermentative production of vitamin $B_{12}$. Since, however, they are of natural origin, their costs and amounts of supply are not always stable, and these materials are not commercially suitable for the fermentative production of vitamin $B_{12}$. The use as carbon sources of alcohols and ketones which are readily available as petrochemical products at low costs and supplied in constant amounts is very advantageous for commercial operations. When water-immiscible or water-insoluble hydrocarbons are utilized as carbon sources, the separation of vitamin $B_{12}$-containing cells from the culture broth is extremely difficult because of the hydrocarbons remaining in it. When methanol is used as a carbon source, this trouble with the separation of the product can be avoided because of its good water solubility. But in cultivation under aeration, the amount of methanol that volatilizes increases since it has a low boiling point. This is inconvenient for the cultivation to be operated stably.

The present inventors extensively worked so as to develop a process for fermentatively producing vitamin $B_{12}$ which can overcome the disadvantages of the conventional techniques. The work led to the successful isolation of Arthrobacter hyalinus, a novel strain belonging to the genus Arthrobacter. It has been found that this vitamin $B_{12}$-producing microorganism can be cultivated advantageously in a culture medium containing as a carbon source at least one compound selected from alcohols containing 2 or 3 carbon atoms and ketones which are readily available as petrochemical products at low costs and supplied in constant quantities and which are not lost by volatilization during aerating cultivation; and that this microorganism has the ability to produce vitamin $B_{12}$ in large quantities.

The inventors also found that the same advantage can be achieved by cultivating known vitamin $B_{12}$-producing microorganisms of the genus Arthrobacter in a culture medium containing at least one compound selected from the group consisting of alcohols containing 2 or 3 carbon atoms and ketones as a carbon source.

It is an object of this invention therefore to provide a process for producing vitamin $B_{12}$ with commercial advantage by a fermentation technique utilizing vitamin $B_{12}$-producing microorganisms of the genus Arthrobacter.

Another object of this invention is to disclose the existence of a novel vitamin $B_{12}$-producing strain of the genus Arthrobacter which can be utilized in the fermentative production of vitamin $B_{12}$, and to contribute further to the art to which the invention pertains.

The above and other objects and advantages of the invention will become more apparent from the following description.

Examples of the known vitamin $B_{12}$-producing microorganisms of the genus Arthrobacter include Arthrobacter simplex (ATCC 6946), Arthrobacter tumescens (deposited at Institute for Fermentation, Osaka, Japan under deposit number IFO 12960), and Arthrobacter globiformis (ATCC 8010). The novel strain Arthrobacter hyalinus isolated by the present inventors was deposited in Fermentation Research Institute, Agency of Industrial Science and Technology, Japan under deposit number FERM-P 3125. This novel strain was also deposited in American Type Culture Collection under deposit number ATCC 31263.

Arthrobacter hyalinus possesses the following microbiological properties which are not found in the description of "Bergey's Manual of Determinative Bacteriology", 7th edition. Accordingly, it was identified as a novel strain belonging to the genus Arthrobacter, and so named.

MICROBIOLOGICAL PROPERTIES OF ARTHROBACTER HYALINUS

1. Morphological properties
    Morphology: in the early stage of cultivation, long curved rods having a size of 0.8 × 4–5 microns, and some of them V-form; in the later stage of cultivation, changed to short rods with a size of 1.2 × 1.5 microns.
    Motility: none
    Gram staining: positive or negative
    Formation of spores: none
2. Properties in cultivation
    Nutrient agar plate culture: peripheral edge erose, umbonate, transparent, moistly shining
    Nutrient agar slant culture: growth poor, filiform, transparent, moistly shining
    Nutrient liquid culture: turbid
3. Physiological properties
    Growth temperature: 25°–35° C.
    Growth pH: 6–9
    Oxygen demand: facultatively anaerobic
    Liquefaction of gelation: none Litmus mill: slightly turned alkaline, and very slowly peptonized
Indole: not generated
Hydrogen sulfide: generated
Reduction of nitrates: none
Catalase: not formed
Urease: formed
Acid fastness: negative
Decomposition of starch: none
Fermentability of sugars: Neither acids nor gases are generated from glycerin, arabinose, xylose, fructose, galactose, glucose, mannitol, sorbitol, lactose, maltose, sucrose and raffinose.
Asparagine: not decomposed
Citric acid: not decomposed According to the present invention, a vitamin $B_{12}$-producing microorganism of the genus Arthrobacter is cultivated in the culture medium, and vitamin $B_{12}$ can be separated directly or indirectly from the culture broth.

The culture medium used in this invention may contain inorganic salts and antifoamers in addition to carbon and nitrogen sources.

In the process of this invention, at least one compound selected from the group consisting of alcohols with 2 or 3 carbon atoms and ketones is incorporated as a carbon source. Examples of preferred carbon sources are ethyl alcohol, n-propanol, i-propanol, ethylene glycol, propylene glycol, glycerin and acetone. Other carbon sources such as n-paraffin, carbohydrates, and oils and fats can be used together. Frequently, the conjoint use of the other carbon sources is expected to increase the output.

Nitrogen sources to be incorporated in the culture medium include, for example, corn steep liquor, yeast extract, peptone, chopped fish powders, vegetable proteins, soybean wastes, a dry powder of malt whiskey waste (SUNGROWTH, a product of Sun Growth Co., Ltd.), ammonium salts, nitrate salts, and urea.

Examples of the inorganic salts are cobalt salts, phosphate salts, magnesium salts, manganese salts, zinc salts, calcium salts, molybdenum salts, and copper salts. Addition of manganese salts can be omitted where their presence is detrimental to the production of vitamin $B_{12}$. Furthermore, a vitamin $B_{12}$ precursor such as 5,6-dimethyl benzoimidazole can be added to the culture medium as a promotor for vitamin $B_{12}$ production.

The composition of the culture medium can be varied as needed, and the desired ingredients may be added supplementally during cultivation. For example, the carbon sources may be added successively in small portions so as not to cause a decrease in the rate of growth in the logarithmically growing phase. They can also be added successively in small portions in the vitamin $B_{12}$-producing phase.

Cultivation is carried out under aerobic conditions, for example, with aeration and stirring. The cultivation temperature is generally about 20° to about 40° C., and the pH is about 4 to about 9.5. The cultivation time is usually from about 2 to 8 days, and can be suitably changed according to changes in the other cultivation conditions.

Separation of vitamin $B_{12}$ from the fermentation product can be performed in the same way as in the prior art. Since vitamin $B_{12}$ builds up mainly within the cells of the microorganism, it is desirable first to centrifuge the culture broth so as to obtain the cells. When it is desired to separate it as a cyano-type vitamin $B_{12}$, a cyanogen ion is added to the cells, and after adjusting the pH to 5 with an acid such as sulfuric acid, the mixture is maintained at 80° to 100° C. in an aqueous medium. Where it is desired to separate it from the culture broth as a coenzyme-type vitamin $B_{12}$ (5,6-dimethyl benzimidazole cobamide coenzyme) and hydroxyl-type vitamin $B_{12}$, the cells may be extracted in a customary manner with a solvent such as methanol, ethanol, acetone or pyridine in an aqueous medium in a dark place. The extracting temperature may be room temperature, but the extraction system may be heated to about 100° C.

Vitamin $B_{12}$ extracted from the culture broth can be purified by a suitable combination of known means such as extraction with phenol, adsorption with activated carbon, or column chromatography using an ion exchange resin or cellulose.

The following Examples illustrate the present invention more specifically.

EXAMPLE 1

Arthrobacter hyalinus (FERM-P 3125; ATCC 31263 was inoculated in a test tube with an inside diameter of 20 mm containing 10 ml of a sterilized culture medium containing deionized pure water and per liter of the water, 10 ml of isopropanol, 3 g of peptone, 1 g of yeast extract, 3 g of $NH_4NO_3$, 1.5 g of $Na_2HPO_4.12H_2O$, 0.4 g of $KH_2PO_4$, 0.5 g of $MgSO_4.7H_2O$, 10 mg of $FeSO_4.7H_2O$, 10 mg of $MnSO_4.4H_2O$, 10 mg of $ZnSO_4.7H_2O$, 5 mg of $Co(NO_3)_2$, 50 μg of $CuSO_4.5H_2O$, 10μg of $MoO_3$ and 5 g of $CaCO_3$. It was cultivated at 30° C. for 5 days with shaking. The concentration of vitamin $B_{12}$ produced in the culture broth was 200 μg/liter.

EXAMPLE 2

Example 1 was repeated except that the manganese salt was omitted from the culture medium. The concentration of vitamin $B_{12}$ produced was 350 μg/liter.

EXAMPLE 3

Example 2 was repeated except that each of the various carbon sources shown in Table 1 was used instead of the isopropanol. The concentrations of vitamin $B_{12}$ produced, and the concentrations of the cells were determined, and the results are shown in Table 1.

Table 1

| | Production of vitamin $B_{12}$ by Arthrobacter hyalinus | |
|---|---|---|
| Carbon source | Cells ($OD_{610\,m\mu}$) | Vitamin $B_{12}$ (μg/liter) |
| Ethyl alcohol | 12 | 370 |
| n-Propanol | 17 | 240 |
| Ethylene glycol | 3.4 | 92 |
| Propylene glycol | 5.3 | 81 |
| Glycerin | 4.0 | 83 |
| Acetone | 7.6 | 180 |

* $OD_{610\,m\mu}$ = optical density measured with light having a wavelength of 610 mμ

EXAMPLE 4

Example 2 was repeated except that 3.0 g of a dry powder of malt whiskey waste (SUNGROWTH, a product of Sun Growth Co., Ltd.) was used instead of the peptone. The concentration of vitamin $B_{12}$ produced was 420 μg/liter.

EXAMPLE 5

Arthrobacter hyalinus was inoculated in three 500 ml. conical flasks each containing 100 ml of a sterilized culture medium containing 10 ml of isopropanol, 3 g of peptone, 1 g of yeast extract, 3 g of $NH_4NO_3$, 1.5 g of $Na_2HPO_4.12H_2O$, 0.4 g of $KH_2PO_4$, 0.5 g of $MgSO_4.7H_2O$, 10 mg of $FeSO_4.7H_2O$, 10 mg of $ZnSO_4.7H_2O$, 5 mg of $Co(NO_3)_2$, 50 µg of $CuSO_4.5H_2O$, 10 µg of $MoO_3$, and 5 g of $CaCO_3$, and cultivated at 30° C. for 2 days with shaking. The culture broth obtained was reserved for use as a seed.

Five liters of a culture medium composed of deionized pure water, and per liter of the water, 10 ml of isopropanol, 3 g of peptone, 1 g of yeast extract, 9 ml of corn steep liquor, 12 g of $NH_4NO_3$, 1.5 g of $Na_2HPO_4.12H_2O$, 1.9 g of $KH_2PO_4$, 0.5 g of $MgSO_4.7H_2O$, 10 mg of $FeSO_4.7H_2O$, 10 mg of $ZnSO_4.7H_2O$, 5 mg of $Co(NO_3)_2$, 50 µg of $CuSO_4.5H_2O$, 10 µg of $MoO_3$, 6 g of $CaCO_3$ and 0.5 ml of an antifoamer was prepared in a 10-liter fermentation tank, and sterilized. Then, 300 ml of the seed prepared as set forth above was inoculated in the culture medium, and cultivated at 32° C. for 60 hours with stirring at 600 rpm while passing aseptic air at a rate of 2.5 liters/min. During the course of fermentation, the cells were grown for 30 hours in the logarithmically growing phase while adding isopropanol so that its concentration in the culture broth did not exceed 3.0 ml/liter. Subsequently, in the vitamin $B_{12}$-producing phase, the amount of isopropanol added was controlled so as to maintain the pH of the culture broth at 7-8. The concentration of vitamin $B_{12}$ produced reached 1.100 µg/liter. The amount of isopropanol consumed was 33 ml per liter of the culture broth.

5.3 liters of the resulting culture broth was centrifuged at 10,000 G to separate the cells. Extraction of vitamin $B_{12}$ from the cells and its purification were performed in a customary manner. Specifically, isopropanol was added to the cells in an amount four times the amount of the latter. The mixture was allowed to stand overnight at room temperature in a dark place. The resulting suspension of the cells in isopropanol was centrifuged at 10,000 G to separate the isopropanol extract. The isopropanol was evaporated off from the extract, and the residue was extracted with an 80% aqueous solution of phenol to transfer vitamin $B_{12}$ to the lower phenol layer. The phenol layer was washed once with water, and a mixture of equal volumes of ether and water was added to transfer vitamin $B_{12}$ to the aqueous layer. The resulting aqueous solution of vitamin $B_{12}$ was purified by column chromatography using TEAE cellulose. Fractions containing vitamin $B_{12}$ were concentrated, and acetone was added to afford 2.8 mg of vitamin $B_{12}$ crystals. This vitamin $B_{12}$ was a coenzyme-type vitamin $B_{12}$.

EXAMPLE 6

Arthrobacter hyalinus was inoculated in a test tube with an inside diameter of 20 mm containing 10 ml of a sterilized culture medium consisting of deionized pure water, and per liter of the water, 10 ml of isopropanol, 10 ml of n-paraffin, 3 g of peptone, 3 g of SUN-GROWTH (a dry powder of malt whiskey waste, a product of Sun Growth Co., Ltd.), 3 g of $NH_4NO_3$, 1.5 g of $Na_2HPO_4.12H_2O$, 0.4 g of $KH_2PO_4$, 0.5 g of $MgSO_4.7H_2O$, 10 mg of $FeSO_4.7H_2O$, 10 mg of $ZnSO_4.7H_2O$, 5 mg of $Co(NO_3)_2$, 50 µg of $CuSO_4.5H_2O$ and 10 µg of $MoO_3$, and cultivated at 30° C. for 5 days with shaking. The concentration of vitamin $B_{12}$ produced in the culture broth was 1,240 µg./liter.

EXAMPLE 7

Example 3 was repeated except that Arthrobacter simplex (ATCC 6946) was used instead of the Arthrobacter hyalinus. The concentrations of vitamin $B_{12}$ produced and the concentrations of the cells were determined, and the results are shown in Table 2.

Table 2

| Production of vitamin $B_{12}$ by Arthrobacter simplex | | |
|---|---|---|
| Carbon source | Cells ($OD_{610\,m\mu}$) | Vitamin $B_{12}$ (µg/liter) |
| Ethyl alcohol | 3.2 | 51 |
| n-Propanol | 10.0 | 103 |
| i-Propanol | 3.1 | 84 |
| Ethylene glycol | 3.2 | 92 |
| Propylene glycol | 11.9 | 124 |
| Glycerin | 7.7 | 89 |
| Acetone | 3.1 | 134 |
| n-Paraffin | 19.0 | 130 |

EXAMPLE 8

Example 2 was repeated except that Arthrobacter tumescens (IFO 12960) was used instead of the Arthrobacter hyalinus, and 10 ml of glycerin was used instead of the isopropanol. The concentration of vitamin $B_{12}$ produced was 134 µg/liter, and the concentration of the cells was 17.4 ($OD_{610\,m\mu}$).

EXAMPLE 9

Example 2 was repeated except that Arthrobacter globiformis (ATCC 8010) was used instead of the Arthrobacter hyalinus, and 10 ml of acetone was used instead of the isopropanol. The concentration of vitamin $B_{12}$ produced was 91 µg/liter, and the concentration of the cells was 2.90 ($OD_{610\,m\mu}$).

In the above Examples, vitamin $B_{12}$ in the culture broth was determined by a microorganism determining method as follows: Potassium cyanide was placed in the diluted culture broth, and after adjusting the pH to 5, the mixture was boiled for 15 minutes to convert vitamin $B_{12}$ to cyanocobalamine. It was then quantitatively determined using Lactobacillus leichmannii (ATCC 7830).

What we claim is:

1. A process for producing vitamin $B_{12}$, which comprises cultivating a vitamin $B_{12}$-producing microorganism of the species Arthrobacter hyalinus under aerobic conditions in a culture medium containing at least one compound selected from the group consisting of ethyl alcohol, n-propanol, 1-propanol and acetone, and separating vitamin $B_{12}$ from the culture broth.

2. A process for producing vitamin $B_{12}$, which comprises cultivating a vitamin $B_{12}$-producing microorganism of the species Arthrobacter hyalinus under aerobic conditions in a culture medium containing at least one compound selected from the group consisting of alcohols of 2 or 3 carbon atoms and acetone, and separating vitamin $B_{12}$ from the culture broth.

3. The process of claim 2 wherein the cultivation is carried out at a temperature of about 20° to about 40° C.

4. The process of claim 2 wherein the cultivation is carried out at a pH of about 4 to about 9.5.

* * * * *